US 8,747,310 B2

(12) United States Patent  
Kimura

(10) Patent No.: US 8,747,310 B2  
(45) Date of Patent: Jun. 10, 2014

(54) METHOD AND APPARATUS FOR ASSESSING THE HEALTH OF AN INFANT BY ESTIMATING AVERAGE GROWTH VELOCITY USING AN EXPONENTIAL MODEL

(75) Inventor: Robert E. Kimura, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 2015 days.

(21) Appl. No.: 11/563,571

(22) Filed: Nov. 27, 2006

(65) Prior Publication Data

US 2007/0100581 A1      May 3, 2007

(51) Int. Cl.
A61B 5/00 (2006.01)
G06F 19/00 (2011.01)

(52) U.S. Cl.
CPC ....... *G06F 19/3487* (2013.01); *A61B 2503/045* (2013.01)
USPC ........................................................ 600/300

(58) Field of Classification Search
USPC ................................. 600/300–301; 705/2–4
See application file for complete search history.

(56) References Cited

U.S. PATENT DOCUMENTS

| | | | |
|---|---|---|---|
| 4,100,602 A | 7/1978 | Shapiro | |
| 4,709,331 A | 11/1987 | Barkett et al. | |
| 6,188,570 B1 | 2/2001 | Borkowski | |
| 6,193,654 B1 * | 2/2001 | Richardson et al. | 600/300 |
| 6,273,727 B1 | 8/2001 | Ramsay et al. | |
| 6,454,729 B1 * | 9/2002 | Jacobs et al. | 600/587 |
| 6,636,880 B1 | 10/2003 | Bera | |
| 6,853,949 B2 * | 2/2005 | Honda | 702/173 |
| 6,944,638 B1 | 9/2005 | Putnam | |
| 7,909,763 B2 * | 3/2011 | Abel | 600/300 |
| 2006/0287891 A1 * | 12/2006 | Grasso et al. | 705/3 |
| 2007/0021979 A1 * | 1/2007 | Cosentino et al. | 705/2 |
| 2007/0161870 A1 * | 7/2007 | Abel | 600/300 |

OTHER PUBLICATIONS

Patel et al. "Accuracy of Methods for Calculating Postnatal Growth Velocity for Extremely Low Birth Weight Infants" Dec. 6, 2005, Pediatrics: Official Journal of the American Academy of Pediatrics vol. 116, pp. 1466-1472.*
Patel et al, "Accuracy of Methods for Calculating Postnatal Growth Velocity for Extremely Low Birth Weight Infants," Jul. 27, 2006.

* cited by examiner

*Primary Examiner* — Bill Thomson
*Assistant Examiner* — Bobby Soriano
(74) *Attorney, Agent, or Firm* — Brinks Gilson & Lione

(57) ABSTRACT

The invention covers a method and apparatus for assessing the health of an infant by accurately estimating the average growth velocity of the infant. The invention employs an exponential model to estimate growth velocity based on at least two weight measurements from different days of life of an infant. The exponential model provides the accuracy and ease of use that are lacking in current methods applied to growth research. The exponential model has numerous features that make it a desirable and powerful model, i.e., (1) it is extremely accurate; (2) it is simple to use, requiring only weight and day of life at 2 time points; (3) it is robust under various testing conditions; and (4) it is unaffected by clinical factors found commonly among ELBW infants, which allows its broad application for the study of infant growth. The exponential model closely approximates the accurate standard GVs, regardless of starting point or time interval used. An exponential model assumes that growth occurs at a fraction of the previous weight. Although growth does not occur at a constant rate of change, the average GV smoothes the variability in weight gain observed clinically, thereby providing an estimate of a theoretically constant rate of change. The average growth velocity is thus a useful in assessing the health of an infant.

20 Claims, 3 Drawing Sheets

METHOD AND APPARATUS FOR ASSESSING THE HEALTH OF AN INFANT BY ESTIMATING AVERAGE GROWTH VELOCITY USING AN EXPONENTIAL MODEL

FIELD OF INVENTION

The subject patent is in the area of health care, specifically techniques for assessing health of an individual and determining proper care practices. It is intended to be used primarily as a tool for assessing the health of an infant through determination of an estimated average growth velocity of the infant and using this estimated average growth velocity to derive other relevant information useful in assessing health.

BACKGROUND

In the United States, at least 22845 extremely low birth weight infants (ELBW, birth weight<1000 g) were born in the most recent year for which data are available. These infants account for a significant percentage of the mortality associated with prematurity, and suffer the majority of short and long-term morbidities, including poor postnatal growth. In fact, most of these infants are below the 10th percentile for weight at discharge when compared to intrauterine reference fetuses of similar gestational ages. Several investigators have demonstrated that postnatal growth is influenced by the severity of coexisting morbidities that affect infant nutritional and metabolic status. At least two previous publications (e.g., Ehrenkranz et al., Wright et al., etc.) showed that infants without major morbidities grew at a significantly faster rate than the less healthy infants. Another publication, (e.g., Radmacher et al.) reported a significantly faster rate of growth in infants without bronchopulmonary dysplasia (BPD) than for those with BPD.

Thus, the measurement of postnatal growth is central in the clinical care and research for ELBW infants because it provides an indirect measure of overall infant health, nutritional adequacy, and care practices. Although various growth measurements are used in clinical practice, growth velocity (GV, g/kg/d) is the most frequently reported measure in growth research in ELBW infants. Average GV is an attractive measure for research purposes because it summarizes the infant's weight gain over a desired time interval, often smoothing the variability seen in daily weight measures. Average GV is used to guide day-to-day decisions in the care of ELBW infants, such as determining the feeding regimen. Postnatal GV is also used frequently in research as a dependent variable to assess the safety and efficacy of interventions, particularly nutritional regimens, as well as an independent variable to predict important outcomes such as neurocognitive development, IQ, and the risk of adult-onset diseases.

However, the calculation of GV on a daily basis from actual weight measurements and averaging those measurements over the desired time interval is extremely labor-intensive. Moreover, the ability of many physicians to calculate GV is limited by their unfamiliarity with scientific calculators. Therefore, various differing methods for estimating average GV have been employed in studies that have reported GV as a dependent variable. Some investigators used absolute weight gain over a specified time interval, without normalizing data for either initial infant weight or time. Others used average daily weight gain calculated from weight measurements over a specified time interval, without normalizing data for initial infant weight. Other researchers estimated average GV through the use of linear regression equations that predicted weight as a function of time. Still others reported GV but did not specify the formula used for estimation. Finally, some investigators used z scores to compare birth weight (BW) and postnatal weight at specified times with in utero weight at similar gestational age. With such widely varying procedures for estimating average GV, the results of therapeutic practices cannot be compared across settings and studies.

These different mathematical models yield varying estimates of average GVs, compared with actual GVs. The magnitude of error in estimating GV with these methods was dependent on the starting point and time intervals of the measurement. There are large percentage differences between estimated GV and the accurate standard GV with the 2-point BW and linear BW models and moderate differences with the 2-point average weight and linear average weight models.

The discrepancy in results obtained through these various methods makes comparisons across studies difficult to perform. Although consistently applying the same starting point and time interval may facilitate comparisons, it may not be an appropriate option because the use of each starting point has its own merits. Evaluation of growth starting from birth includes a gross assessment of disease severity, because sicker infants grow more slowly and regain BW later. In contrast, evaluating growth starting from regaining BW measures the adequacy of the nutritional regimen, with the caveat that chronic and late-onset illnesses (e.g., sepsis or chronic lung disease) may affect this growth rate. Therefore, it may be difficult to standardize the starting point and time interval, because these would vary with the particular research question. Moreover the accuracy of these methods of estimating average GV is affected by factors observed commonly among ELBW infants, such as BW, chronic lung disease and longer hospital stays. Therefore, there is a great need for an accurate and uniform method of estimating average GV.

SUMMARY OF THE INVENTION

An object of the present invention is to solve the deficiencies of the aforementioned linear methods of estimating average GV and provide for an accurate and uniform way of estimating average GV of an individual. "Individual" as used herein includes both human and other animals and both infants and adults. It has now been discovered and confirmed by studies that the current discrepancies and inaccuracies in calculation methods found in the growth literature may be resolved by using an exponential model for estimating GV normalized for weight. Illustrated embodiments of the invention employ said exponential model to estimate growth velocity based on at least two weight measurements from different days in the life of an infant. The exponential model provides the accuracy and ease of use that are lacking in current methods applied to infant growth research. The exponential model has numerous features that make it a desirable and powerful model, i.e., (1) it is extremely accurate; (2) it is simple to use, requiring only weight and day of life at 2 time points; (3) it is robust under various testing conditions; and (4) it is unaffected by clinical factors commonly found among ELBW infants, which allows its broad application for the study of infant growth. From a practical perspective, the exponential model is very simple to use, requiring only two weight measurements and the day of life of the weight measurement. The exponential model closely approximates the accurate standard GVs, regardless of starting point or time interval used. Although days of life from birth may be the measurement standard used, fractions of days and/or hours and/or minutes may also be appropriate in some cases. An exponential model assumes that growth occurs at a fraction of the previous weight. Although growth does not occur at a constant rate of change, the average GV smoothes the variability in weight gain observed clinically, thereby providing an estimate of a theoretically constant rate of change.

DETAILED DESCRIPTION

The present invention recognizes that two weight measurements from different days can be used to estimate the average growth velocity of an individual using an exponential model.

Figure 1:
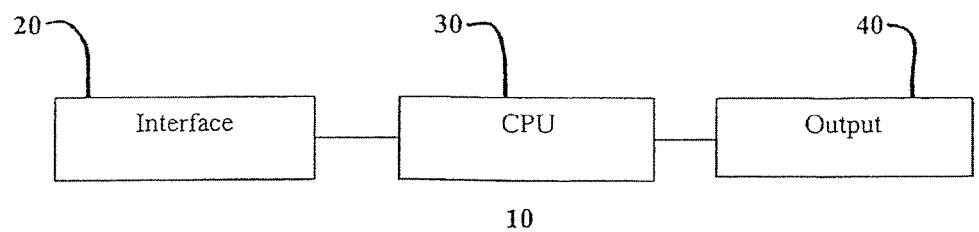
FIG. 1 illustrates an apparatus to determine average growth velocity in accordance with an illustrated embodiment.

FIG. 1 depicts a system 10 that estimates the average growth velocity in accordance with an illustrated embodiment of the invention. Referring to FIG. 1, weight measurements and the respective day of life of those weight measurements can be entered into the CPU 30 through an interface 20 configured to communicate data to the CPU 30. The interface 20 may be any device capable of transmitting data to the CPU 30, including but not limited to a keypad, keyboard, or any other interface designed for manual input of the day of life and corresponding weight measurements. Alternatively, the interface 20 may be integrated with a weight measurement and input device. For example, in one embodiment, the CPU 30 may be connected physically or wirelessly to a weight measurement device which serves as the interface 20 to communicate day of life and corresponding weight measurements to the CPU 30. In another embodiment, a keypad or keyboard may serve as the interface 20 through which a user manually enters identifiers of the days of life and corresponding weight measurements to be communicated to the CPU 30. The CPU 30 employs an equation according to an exponential model to determine estimated average growth velocity based on the data it receives from the interface 20. The CPU 30 can also be configured to use the determined estimated average growth velocity to further derive a model curve of estimated weight versus time or to estimate the day of life an infant attains a specified weight or the weight an infant attains on a specified day of life as illustrated in FIG. 2 and FIG. 3.

Figure 2:
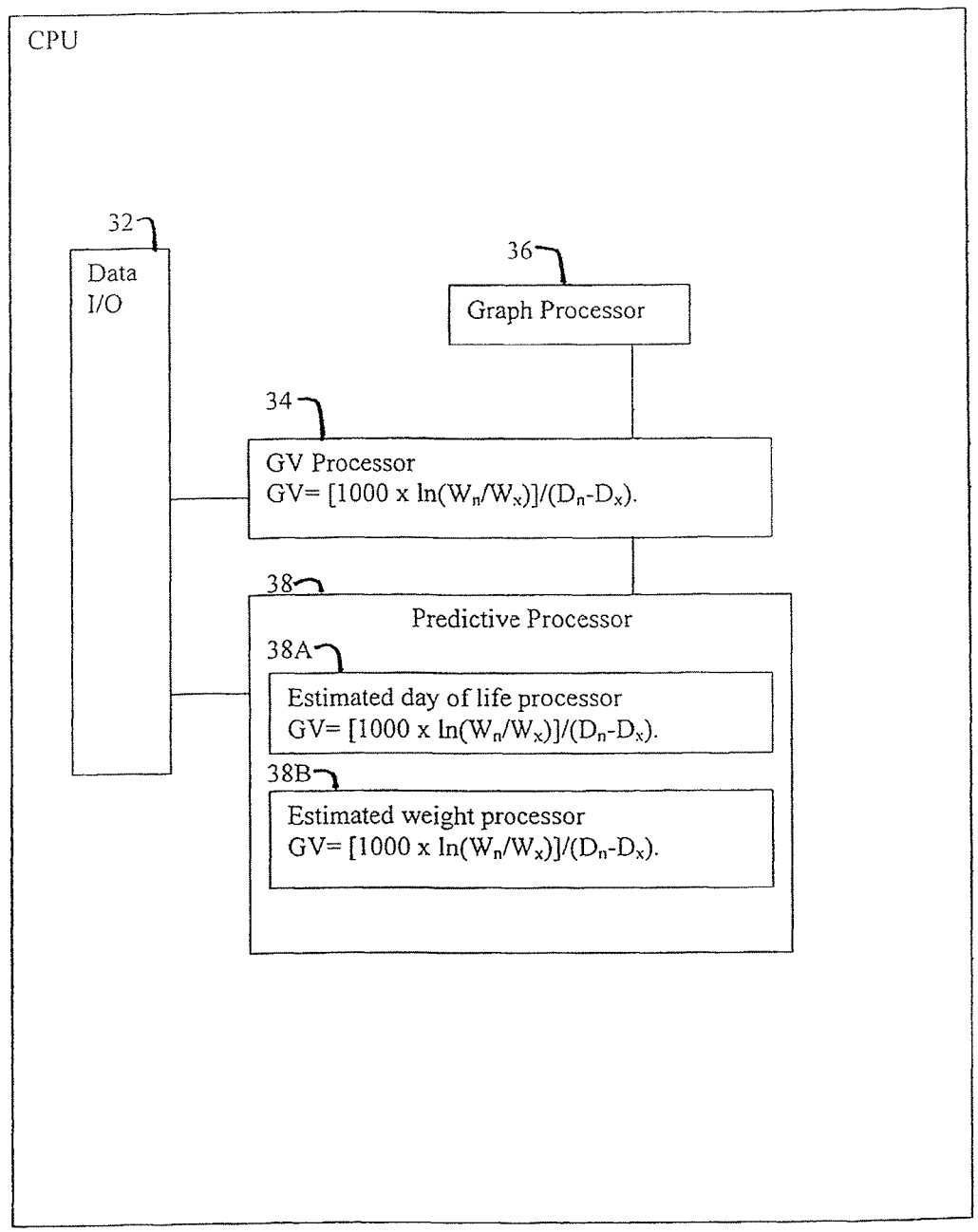
FIG. 2 depicts the CPU of FIG. 1 in accordance with an illustrated embodiment.
Figure 3:
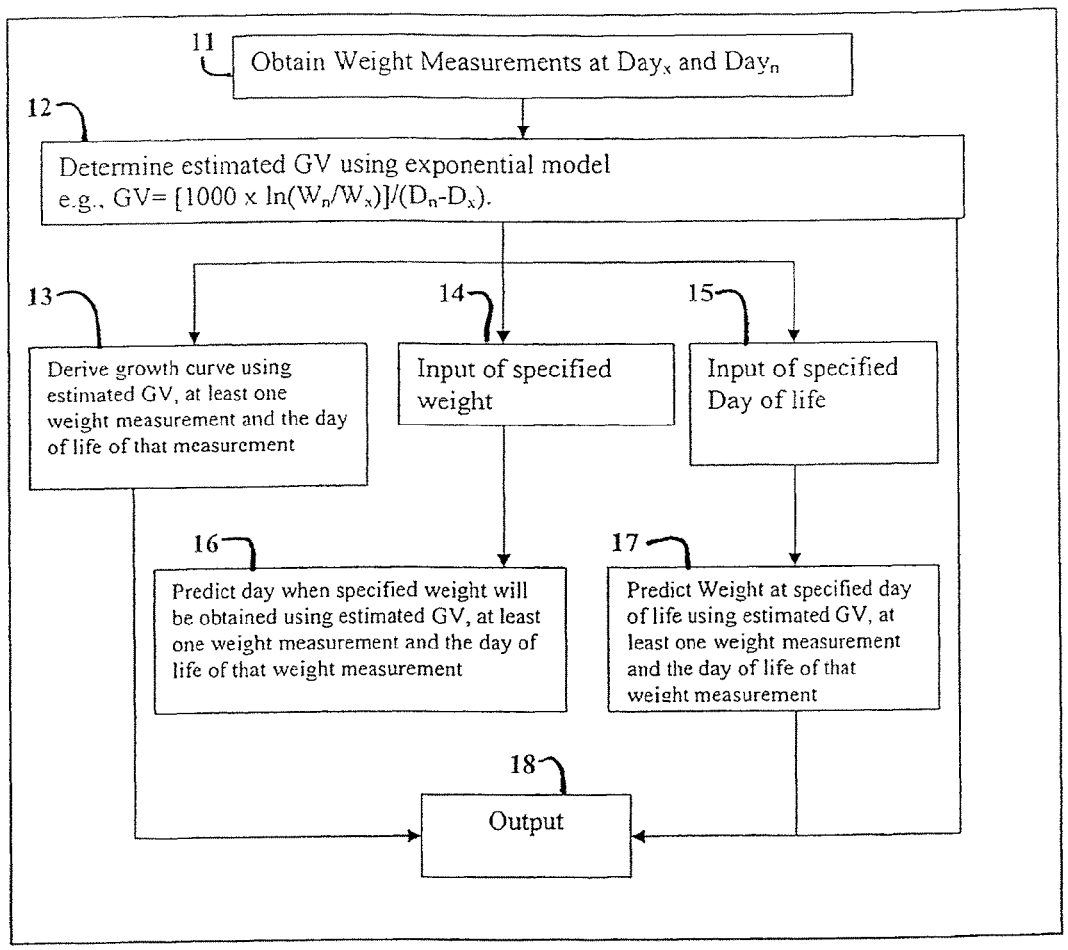
FIG. 3 is a flow chart illustrating the process steps that may be used by the system of FIG. 1 in accordance with an illustrated embodiment.

FIG. 2 depicts one embodiment of a CPU 30 configured to estimate the average growth velocity of an infant. In this example, the CPU 30, includes an I/O processing unit 32; a growth velocity processor 34 to determine the estimated average growth velocity of an infant based on at least two weight measurements and the days of life of those weight measurements; a graph processor 36 configured to derive a model curve based on the estimated average growth velocity, at least one weight measurement, and the day of life of that measurement; and a predictor processor 38 configured to estimate the weight an infant attains on a specified day or the day an infant attains a specified weight.

The I/O unit 32 of the CPU 30 receives the data from the interface 20 which can then communicate data to the growth velocity processor 34. The I/O unit 32 can also communicate data (e.g., a growth velocity) from the growth velocity processor 34 to the predictor processor 38 or the graph processor 36. The I/O unit 32 may also include a memory that may be configured to store day of life and corresponding weight data for further processing or transmission to another device or media.

The growth velocity processor 34 receives day of life and corresponding weight measurements from the I/O unit 32 and employs an equation according to an exponential model to determine estimated average growth velocity based on the data it receives. In one embodiment of the invention, the growth velocity processor 34 determines estimated average growth velocity by executing a set of computer instructions based upon the following equation: $GV=[1000\times\ln(W_n/W_x)]/(D_n-D_x)$, wherein GV is the estimated average growth velocity; $W_x$ is the weight at day of life $D_x$; and $W_n$ is the weight at a subsequent day of life, $D_n$.

The CPU 30 can also include a graph processor 36. The graph processor 36 is configured to receive the estimated average growth velocity determined by the growth velocity processor 34 and a day of life and corresponding weight measurement for at least one day of life of an infant to derive a model curve of past, present or future weights. In one embodiment, the graph processor 36 derives the curve by executing a set of computer instructions based upon the same equation described above, namely $GV=[1000\times\ln(W_n/W_x)]/(D_n-D_x)$. The estimated average growth velocity determined by the growth velocity processor 34 is substituted for GV; a day of life and corresponding weight measurement are substituted for $D_x$ and $W_x$, respectively; $W_n$ is then calculated for a plurality of days of life sufficient to create enough data points to plot the model curve on a graph of weight versus day of life.

In one embodiment, the CPU 30 can also include a predictor processor 38 configured to receive the estimated average growth velocity determined by the growth velocity processor 34, weight measurements, and the day of life of said weight measurements. The predictor processor 38 can also be configured to receive input of either a specified past, present or future day of life or a specified past, present or future weight.

The predictor processor 38 can include an estimated day of life processor 38A configured to estimate the day of life that an infant attains a specified weight. In one embodiment, the estimated day of life processor 38A can use the specified weight received from the predictor processor 38 or the Data I/O unit 32, the estimated average growth velocity determined by the growth velocity processor 34, one other weight measurement, and the time of that weight measurement to estimate the day of life that an infant attains the specified weight using an equation according to an exponential model. In one embodiment, the estimated day of life processor 38A determines the day of life that an infant attains a specified weight by executing a set of computer instructions based upon the same equation used to determine the estimated average growth velocity described above.

For example, to determine the day of life on which a specified weight is attained, the estimated day of life processor 38A may use the equation described above, $GV=[1000\times\ln(W_n/W_x)]/(D_n-D_x)$, substituting the estimated average growth velocity determined by the growth velocity processor 34 for GV; substituting a day of life and corresponding weight measurement for $D_x$ and $W_x$, respectively; substituting the specified weight received from the predictor processor 38 or the Data I/O unit 32 for $W_n$; and solving the equation for $D_n$, which represents the day of life that the infant attains the specified weight.

Similarly, the predictor processor 38 may also include an estimated weight processor 38B configured to estimate a weight that an infant attains on a specified day of life. In one embodiment, the estimated weight processor 38B can use the specified day of life received from the predictor processor 38 or the Data I/O unit 32, the estimated average growth velocity determined by the growth velocity processor 34, one other weight measurement, and the time of that measurement to estimate the weight an infant attains on a specified day of life using an equation according to an exponential model. In one embodiment, the estimated weight processor 38B executes a set of computer instructions based on the equation used to determine the estimated average growth velocity described above.

For example, to determine the weight an infant attains on a specified day of life, the estimated weight processor 38B may use the equation described above, $GV=[1000\times\ln(W_n/W_x)]/(D_n-D_x)$, substituting the estimated average growth velocity determined by the growth velocity processor 34 for GV; substituting a day of life and corresponding weight measurement for $D_n$ and $W_x$, respectively; substituting the specified day of life received from the predictor processor 38 or the Data I/O unit 32 for $D_n$; and solving the equation for $W_n$, which represents the estimated weight an infant attains on the specified day of life.

The CPU 30 can communicate the estimated average growth velocity determined by the growth velocity processor 34; the model curve derived from the graph processor 36; or the day of life or weight values determined by the predictor processor 38 to an output 40. The output 40 can be any means of conveying information, such as a liquid crystal display (LCD), printer, light emitting diodes (LEDs), sonic alarms, vibration, radio frequency signals, electrical signals, or infrared signals. The output 40 can be integrated with the CPU 30, locally located and connected to the CPU 30, or can be remotely located and connected to the CPU 30 through any system capable of transmitting data to a remote location, such as a wireless network, intranet, or internet. The CPU 30 may also be configured to store data or electronically communicate data to another device for data storage or further processing.

FIG. 3 depicts the process steps that may be used by the system of FIG. 1 to determine an estimated average growth velocity and optionally utilizing that estimated average growth velocity to calculate additional information to aid in the assessment of health of an infant.

In the illustrated embodiment, weight measurements of an infant are determined on a plurality of days of life 11 of that infant. The day of life of an infant is the number of days which has passed since the birth of the infant, counting the day of birth as the 1st day of life. Weight measurements for at least two different days of life of an infant can be obtained through any device capable of accurately measuring weight. The day of life and corresponding weight measurements are used to determine the estimated average growth velocity by executing a set of computer instructions based on an equation according to an exponential model 12. In one embodiment, the estimated average growth velocity is determined by employing the following equation: $(GV=[1000\times\ln(W_n/W_x)]/(D_n-D_x)$, wherein GV is the estimated average growth velocity; Wx is the weight of the infant at day of life $D_x$; and $W_n$ is the weight of the infant at a subsequent day of life, $D_n$ 12.

The estimated average growth velocity may be communicated to an output 18. The estimated average growth velocity may also be used with at least one day of life and corresponding weight measurement to derive a model curve 13. For example, in one embodiment, the curve is derived by employing the same equation used to determine the estimated average growth velocity $GV=[1000\times\ln(W_n/W_x)]/(D_n-D_x)$ 13. The previously determined estimated average growth velocity is substitute for GV in the above equation; a day of life and corresponding weight measurement are substituted for $D_n$ and $W_x$, respectively; $W_n$ is then calculated for a plurality of days of life sufficient to create enough data points to plot the model curve on a graph of weight versus day of life 13. The model curve may then be communicated to an output 18.

The previously determined estimated average growth velocity 12 may also be used to estimate the day of life an infant attains a specified weight or the weight an infant attains on a specified day of life by employing an equation according to an exponential model 14-17. In one embodiment, this can be accomplished by using the equation to estimate average growth velocity describe above, namely $GV=[1000\times\ln(W_n/W_x)]/(D_n-D_x)$.

For example, to determine the day of life on which a specified weight is attained, a specified weight is input 14, and the day of life on which an infant attains that weight is estimated using the above equation, substituting the estimated average growth velocity for GV; substituting a day of life and corresponding weight measurement for $D_n$ and $W_x$, respectively; substituting the specified weight for $W_n$; and solving the equation for $D_n$, which represents the day of life that the infant attains the specified weight 16. Similarly, to determine the weight an infant attains on a specified day of life, a specified day of life is input 15, and the weight an infant attains on that specified day of life is estimated using the above equation, substituting the estimated average growth velocity for GV; substituting a day of life and corresponding weight measurement for $D_n$ and $W_x$, respectively; substituting the specified day of life for $D_n$; and solving the equation for $W_n$, which represents the weight an infant attains on the specified day of life 17. These estimated values may then be communicated to an output for display or transmission to other devices 18. While FIG. 3 is a flow chart representing the process steps that may be achieved by the system 10, the process steps can also illustrate subroutines that may be carried out by the CPU 30 of FIG. 2.

Aside from the determination of the various values described above, the present invention may also be useful to provide an estimate of the weight of an infant on a given day where no actual weight measurement has been recorded. This could be useful when comparison studies call for a comparison of weight on a specific day for which a weight measurement of one or more of the subjects is unavailable. This present invention may also have applications in assessing when a health condition affecting growth rate has occurred and determining appropriate treatment. For example, the optimal treatment for many ailments may vary depending on the stage and severity of the ailment. The present invention may be used to determine the onset of an adverse health condition and thereby aid in determination of the appropriate treatment.

It should be evident to persons skilled in the art that the methods and apparatus disclosed have wider application than the methods specifically described above. These methods are not anticipated or disclosed in the prior art. These unique methods are claimed in addition to the described system. A specific embodiment of a method and apparatus for estimating the average growth velocity of an infant according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A method for assessing the growth and health of an infant utilizing a computer, consisting of the steps of:
obtaining data comprising only two weight measurements and time points;
inputting said data into a computer readable medium;
said computer reading the computer readable medium, and determining an estimated average growth velocity of the infant using the following equation: $GV=[1000 \times \ln(W_n/W_x)]/(D_n-D_x)$, wherein GV is the estimated average growth velocity; $W_x$ is a weight of the infant in grams at day of life $D_x$; and $W_n$ is a weight of the infant in grams at a subsequent day of life, $D_n$.

2. The method of claim 1, further comprising communicating the estimated average growth velocity as an output.

3. The method of claim 1, further comprising communicating an estimated weight of an infant on a specified day of life as an output.

4. The method of claim 1, further comprising estimating the day of life an infant attains a specified weight by using the estimated average growth velocity, and said equation.

5. The method of claim 4, further comprising communicating the estimated day of life an infant attains a specified weight as an output.

6. The method of claim 1, further comprising deriving a model curve of estimated weight versus days of life using said estimated average growth velocity, and said equation.

7. The method of claim 6, wherein the model curve is communicated as an output.

8. An apparatus for assessing health of an infant comprising: at least one input for receiving elements comprising only two weight measurements and two time points and a processor which determines estimated average growth velocity based on said weight measurements, the respective time points of said weight measurements and the equation: $GV=[1000 \times \ln(W_n/W_x)]/(D_n-D_x)$, wherein GV is the estimated average growth velocity; $W_x$ is a weight of the infant at day of life $D_x$; and $W_n$ is a weight of the infant at a subsequent day of life, $D_n$.

9. The apparatus of claim 8, further comprising an output for electronically transmitting the estimated average growth velocity.

10. The apparatus of claim 8, further comprising an I/O device which receives a specified day of life of the infant and a processor which estimates a weight of the infant on the specified day of life using the estimated average growth velocity, said two weight measurements, the day of life of each weight measurement, and said equation.

11. The apparatus of claim 10, further comprising an output for electronically transmitting the estimated weight the infant attains on a specified day of life.

12. The apparatus of claim 8, further comprising an I/O device which receives a specified weight and a processor which estimates a day of life the infant attains the specified weight using the specified weight, the estimated average growth velocity, at least one other weight measurement, the day of life of that weight measurement, and said equation.

13. The apparatus of claim 12, further comprising an output for electronically transmitting the estimated day of life an infant attains the specified weight.

14. The apparatus of claim 8, wherein the input further comprises a weight measuring device.

15. The apparatus of claim 8, wherein the input is a key device.

16. The apparatus of claim 8, further comprising a processor which derives a model curve using said estimated average growth velocity, at least one weight measurement and the day of life of the weight measurement.

17. The apparatus of claim 16, further comprising an output which displays the model curve.

18. A method for assessing health of an infant, comprising:
obtaining only two weight measurements of an infant and respective times of the two weight measurements; and
inputting said two weight measurements and times of the two weight measurements into a computer whereby said computer determines an estimated average growth velocity of the infant using only said weight measurements and the respective times of said weight measurements in the following equation: $GV=[1000 \times \ln(W_n/W_x)]/(D_n-D_x)$, wherein GV is the estimated average growth velocity; $W_x$ is a weight of the infant at day of life $D_n$;
and $W_n$ is a weight of the infant at a subsequent day of life, $D_n$.

19. The method of claim 1 wherein said data is wirelessly transmitted to said computer readable medium.

20. The method of claim 18 wherein said data is wirelessly transmitted to said computer.

* * * * *

UNITED STATES PATENT AND TRADEMARK OFFICE
CERTIFICATE OF CORRECTION

| | | |
|---|---|---|
| PATENT NO. | : 8,747,310 B2 | Page 1 of 1 |
| APPLICATION NO. | : 11/563571 | |
| DATED | : June 10, 2014 | |
| INVENTOR(S) | : Kimura | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2118 days.

Signed and Sealed this
Eighth Day of September, 2015

Michelle K. Lee
*Director of the United States Patent and Trademark Office*